(12) United States Patent
Andersen et al.

(10) Patent No.: US 7,054,687 B1
(45) Date of Patent: *May 30, 2006

(54) METHOD AND APPARATUS FOR POSITION AND MOTION SENSING

(75) Inventors: Dean Andersen, San Jose, CA (US); Marc Ryat, Stockholm (SE)

(73) Assignee: Pacesetter, Inc., Sunnyvale, CA (US)

( * ) Notice: Subject to any disclaimer, the term of this patent is extended or adjusted under 35 U.S.C. 154(b) by 624 days.

This patent is subject to a terminal disclaimer.

(21) Appl. No.: 10/232,044

(22) Filed: Aug. 29, 2002

Related U.S. Application Data (62) Division of application No. 09/513,206, filed on Feb. 24, 2000, now Pat. No. 6,477,421.

(51) Int. Cl.
*A61N 1/18* (2006.01)

(52) U.S. Cl. .................................................. 607/19

(58) Field of Classification Search ............... 607/6, 607/9, 17, 18, 19; 600/509, 516, 517, 521
See application file for complete search history.

(56) References Cited

U.S. PATENT DOCUMENTS

| | | | | |
|---|---|---|---|---|
| 4,846,195 A | | 7/1989 | Alt | 128/782 |
| 5,061,928 A | * | 10/1991 | Karema et al. | 341/143 |
| 5,293,169 A | * | 3/1994 | Baumgartner et al. | 341/172 |
| 5,404,877 A | * | 4/1995 | Nolan et al. | 600/484 |
| 5,593,431 A | | 1/1997 | Sheldon | 607/19 |
| 5,649,968 A | | 7/1997 | Alt et al. | 607/19 |
| 5,755,741 A | | 5/1998 | Vogel | 607/19 |
| 5,865,760 A | | 2/1999 | Lidman et al. | 600/509 |
| 5,957,957 A | | 9/1999 | Sheldon | 607/17 |
| 6,097,983 A | * | 8/2000 | Strandberg | 607/9 |
| 6,118,331 A | * | 9/2000 | Yunus et al. | 327/553 |
| 6,326,912 B1 | * | 12/2001 | Fujimori | 341/172 |
| 6,466,821 B1 | * | 10/2002 | Pianca et al. | 607/18 |

OTHER PUBLICATIONS

Aziz, P.M., Sorensen, H.V., van der Spiegel, J., "An Overview of Sigma-Delta Converters". IEEE Signal Processing Magazine. Jan. 1996, pp. 61-84.*

* cited by examiner

Primary Examiner—Jeffrey R. Jastrzab
Assistant Examiner—Alyssa M. Alter
(74) Attorney, Agent, or Firm—Steven M. Mitchell (57) ABSTRACT

An apparatus for extracting activity information and position information from a composite signal generated by a motion sensor includes an analog to digital converter for converting the composite signal from analog to digital format. A wide-band low pass filter having a frequency response of about zero hertz to about ten hertz and a narrow low pass filter having a frequency response of about zero hertz to about 0.5 hertz filter the digitized composite signal. An adder subtracts the output of the narrow-band low pass filter from the output of the wide-band low pass filter. The resulting difference represents information regarding the activity level of the motion sensor, and the output of the narrow-band low pass filter represents information regarding the position of the sensor.

23 Claims, 7 Drawing Sheets

METHOD AND APPARATUS FOR POSITION AND MOTION SENSING

"This is a divisional of application Ser. No. 09/513,206, filed on Feb. 24, 2000 now U.S. Pat. No. 6,477,421."

BACKGROUND OF THE INVENTION

1. Field of the Invention

The present invention is directed to a method and apparatus for extracting position information and activity information from a composite signal generated by a motion sensor. The present invention is particularly applicable to implantable medical devices, such as pacemakers and defibrillators, but the invention is generally applicable any system that utilizes a motion sensor to generate a composite signal containing information about position and activity.

2. Background

Pacemakers are small medical devices that can be implanted in a person with heart disease to provide periodic electrical pulses to stimulate regular beating of the patient's heart. Over the years many improvements have been made to the first pacemaker designs. One such improvement was the addition of a rate adaptive feature. A rate adaptive pacemaker attempts to adjust the rate at which pacing pulses are delivered to the heart to meet the patient's physiological needs.

One method of providing adaptive rate pacing that has proven fairly successful involves use of a motion sensor to determine the patient's level of physical activity. A commonly used motion sensor is an accelerometer, which generates an electrical signal proportional to acceleration. Many accelerometer designs have been developed over the years and have been used in pacemakers to sense the physical activity level of a patient by sensing, for example, the footfalls of a patient as he or she walks, climbs stairs, jogs, or runs. Various methods have been devised for processing the electric signal generated by an accelerometer to determine the physical activity level of the patient.

Clinical studies have shown, however, that a better prediction of the pacing rate needed by a patient can be obtained by considering not only the physical activity level of the patient but also the position of the patient. For example, if a person is walking, the rate at which the person's heart should be paced depends not only on the sensed level of physical activity but also on whether the patient is walking up hill, down hill, or on a level surface. As another example, it is believed that a healthy heart naturally beats slower while the person is lying down than while the person is sitting or standing.

Several schemes have been developed to determine both the patient's activity level and the patient's position. For example, U.S. Pat. No. 5,649,968 to Alt et al. (the '968 patent) discloses a method in which the morphology of a signal generated by a motion sensor is analyzed to determine the patient's position. According to the inventors of the '968 patent, clinical studies show identifiable differences in the morphology of activity signals that depend on the position of the patient. U.S. Pat. No. 5,865,760 to Lidman et al. looks for changes in electrocardiogram data that indicate a change in the patient's position. U.S. Pat. No. 5,593,431 to Sheldon (the '431 patent) discloses use of a so called DC accelerometer that creates a composite signal containing information about both the position and the activity level of the patient. The '431 patent, however, does not disclose an efficient way to separate the position information from the activity level information in the composite signal.

SUMMARY OF THE INVENTION

The instant invention is directed to a method and apparatus for extracting position information and activity information from a composite signal generated by a motion sensor. An analog to digital converter converts the composite signal from analog to digital format. The digitized signal is passed through a low pass filter with a frequency response of about zero hertz to about ten hertz, and the digitized signal is also passed through a narrow low pass filter with a frequency response of about zero hertz to about 0.5 hertz. The output of the narrow low pass filter is subtracted from the output of the low pass filter. The resulting difference represents information regarding the activity level of the motion sensor, and the output of the narrow low pass filter represents information regarding the position of the sensor.

In an alternative embodiment, a sigma-delta converter (also known as a delta-sigma converter) changes the sensor signal from analog to digital format. A sigma-delta converter typically includes a modulator, one or more downsample stages, and one or more anti-alias filters. The modulator typically converts an analog signal into a digital format, and the downsample stages and anti-alias filters typically convert the digital signal into a format that is useful for the particular application. The digitized signal is passed through a narrow low pass filter with a frequency response of about zero hertz to about 0.5 hertz. The output of the narrow low pass filter is subtracted from the output of sigma-delta converter. The resulting difference represents information regarding the activity level of the motion sensor, and the output of the narrow low pass filter represents information regarding the position of the sensor.

DETAILED DESCRIPTION OF THE PREFERRED EMBODIMENT

The present invention is directed to a method and apparatus for extracting position information and activity information from a composite signal generated by a motion sensor that is capable of sensing both position and activity level. As described herein, exemplary embodiments of the invention are incorporated into a rate adaptive pacemaker. The invention is not, however, limited to use with pacemakers, but may be used with any device that utilizes a motion sensor to generate a composite signal containing both position and activity information. Moreover, the following descriptions of preferred embodiments are intended to be exemplary only, and the invention is not intended to be limited to the exemplary embodiments or the manner in which the exemplary embodiments operate or are described herein.

Figure 1:
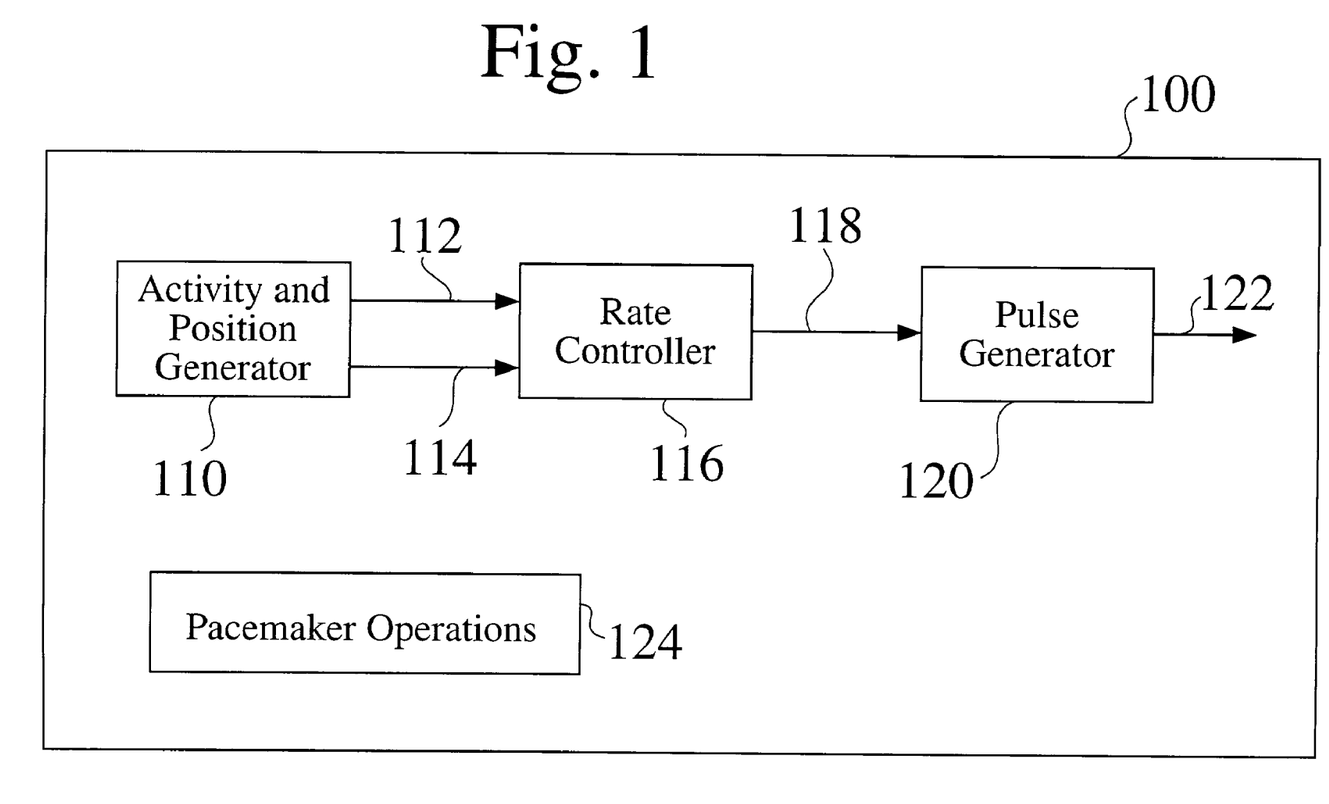
FIG. 1 is a block diagram of an exemplary rate adaptive pacemaker.

FIG. 1 illustrates a rate adaptive pacemaker 100. As is known, rate adaptive pacemakers attempt to adjust the rate at which pacing pulses are delivered to the patient's heart in accordance with the patient's physiological need. The rate adaptive pacemaker 100 illustrated in FIG. 1 includes an activity and position generator 110, a rate controller 116, and a pulse generator 120. Such pacemakers also may include any number of other features that are not pertinent to the instant invention. Apparatus for implementing such features is represented generally in FIG. 1 as pacemaker operations 124.

As shown, the activity and position generator 110 generates at least two signals. The first signal 112 represents the position of the patient in which the pacemaker 100 is implanted. The second signal 114 represents the activity level of the patient. These two signals 112, 114 are used by the rate controller 116 to determine the rate at which pacing pulses should be delivered to the patient's heart. The pulse generator 120 generates pacing pulses at the rate determined by the rate controller 116, and the pacing pulses are delivered to the patients heart (not shown) via electrodes (not shown) as is known in the art. Many rate controllers and pulse generators are known to those skilled in the art, and any suitable rate controller and pulse generator may be used with the present invention.

Figure 2:
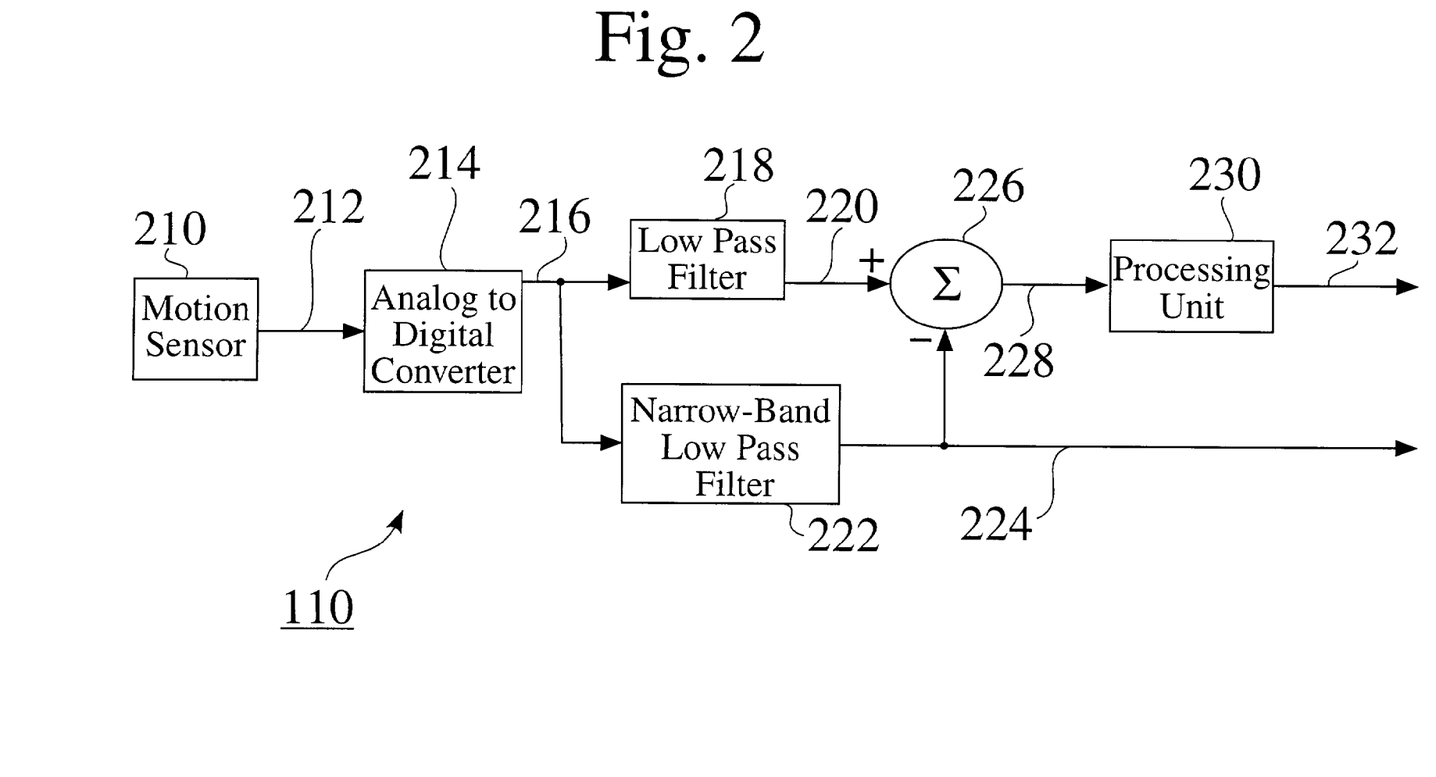
FIG. 2 is a block diagram of an exemplary embodiment of the activity and position generator of FIG. 1.

FIG. 2 illustrates a first embodiment of the activity and position generator 110. A motion sensor 210 generates a composite signal 212 that includes information relating to the patient's level of activity and information related to the patient's position. Many motion sensors for generating such a composite signal are known, and any such sensor may be used with the present invention.

Figure 3:
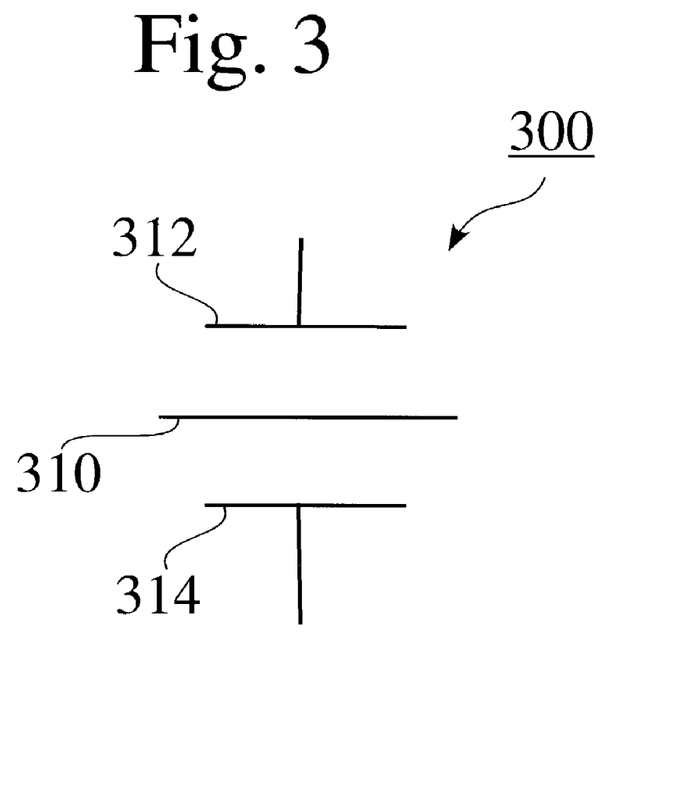
FIG. 3 illustrates a portion of an exemplary MEMS motion sensor.

A microelectomechanical system ("MEMS") is an example of such an motion sensor. Typically, a MEMS sensor comprises one or more small capacitors etched into a piece of silicon. FIG. 3 illustrates a dual capacitor 300. One plate 310 of the dual capacitor 300 is fixed and the other plates 312, 314 are moveable. The moveable plates 312, 314 are deflected by gravity and by accelerations of the motion sensor. While such a MEMS sensor is implanted in a patient, physical activity of the patient causes the moveable plates 312, 314 to vibrate. Using techniques known to those skilled in the art, an alternating current ("AC") electrical signal can be generated that is proportional to the movement of the moveable plates 312, 314. This AC signal contains information about the physical activity level of the patient. For example, such a MEMS sensor generates an AC signal in response to foot falls of a patient while the patient is walking or jogging. Because the moveable plates 312, 314 are also sensitive to gravity, the generated signal will also have a direct current ("DC") component that is proportional to the orientation of the moveable plates 312, 314 with respect to the earth. A MEMS sensor installed in a pacemaker is thus capable of producing a composite signal that contains an AC component relating to the patient's activity level and a DC component relating to the patient's position.

Figure 4:
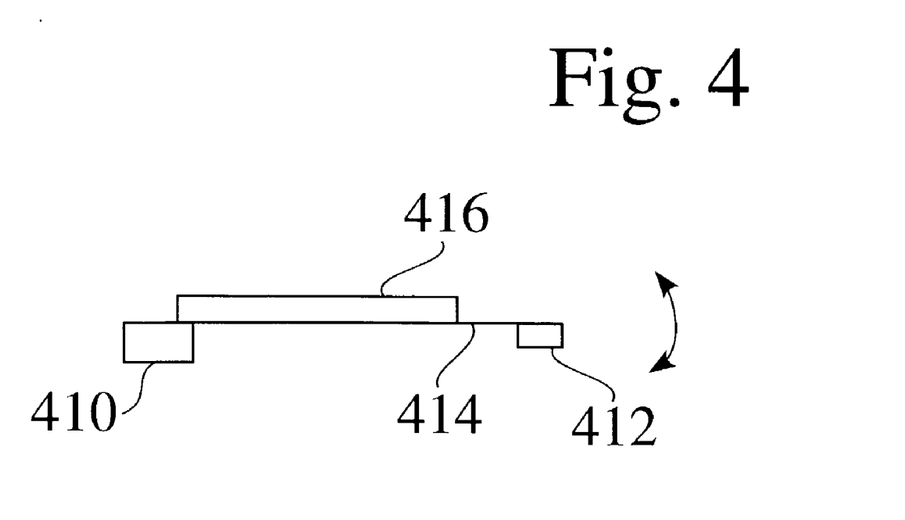
FIG. 4 illustrates an exemplary cantilever motion sensor.

The design of the motion sensor 210 is not critical to the instant invention, and any other suitable design for producing a composite signal containing information about both position and activity may also be used. For example, a cantilever design can also be used. As illustrated in FIG. 4, a basic cantilever design includes a cantilever 414 that is immovably attached at one end to a fixed base 410. A mass 412 is attached to the other end, which is free to move. Gravity pulls the mass 412 toward the earth, causing the cantilever to bend about the fixed base 410. Vibrations also cause the free end of the cantilever to vibrate about the fixed base 410. Piezoelectric material 416 attached to the cantilever 414 create an electrical signal that is proportional to the bending of the cantilever 414. Yet another example of a suitable motion sensor 210 is an enclosure containing an electrolytic fluid and multiple conductors fixed at various positions within the enclosure. An example of such a motion sensor is described in U.S. Pat. No. 5,755,741, which is incorporated herein by reference.

Referring again to FIG. 2, an analog to digital converter 214 converts the composite signal 212 generated by the motion sensor 210 from analog format to digital format. The output of analog to digital converter 214 is a digitized version 216 of the composite signal 212. This digitized composite signal 216 is then filtered by wide-band low pass filter 218 and narrow-band low pass filter 222. Wide-band low pass filter 218 preferably passes frequencies in the range of about zero hertz to about ten hertz. Narrow-band low pass filter 222 preferably passes frequencies in the range of about zero hertz to about 0.5 hertz. Because of the narrow range of frequencies passed by narrow-band low pass filter 222, the output 224 of the narrow-band low pass filter 222 approximates the DC portion of the composite signal 212 created by the motion sensor 210 and therefore can be used to determine the position of the patient. Output 224 can be passed directly to the rate controller 116 as a representation of the position of the patient (signal 112 in FIG. 1), or alternatively, output 224 can be further processed or combined with other signals from other motion sensors before being passed to the rate controller 116.

Adder 226 subtracts signal 224 from signal 220. The resulting output 228 contains frequencies in the range of about 0.5 hertz to about ten hertz from the composite signal 212 created by the motion sensor 210. The output 228 of adder 226 approximates the AC portion of the composite signal 212 created by the motion sensor 210. As is known in the art, the frequency range up to about 10 hertz contains the most relevant information regarding the patient's level of physical activity. The frequency range of the composite signal 212 that exceeds 10 hertz tends to contain mostly noise, spurious signals, or signals that are not relevant to physical activity.

Figure 5:
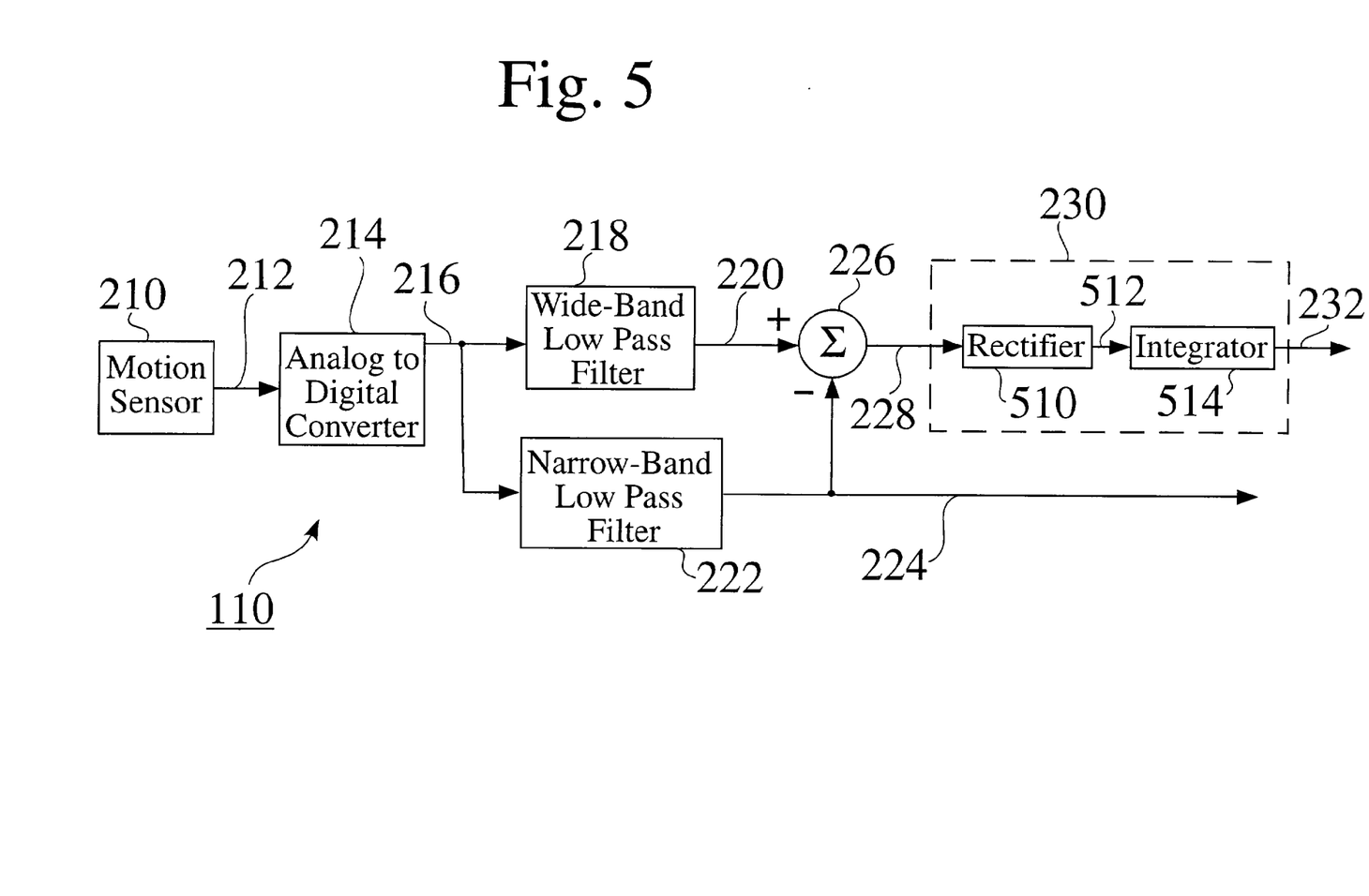
FIG. 5 illustrates a variation of the activity and position generator illustrated in FIG. 2.

Typically, the output 228 of adder 226 is further processed by processing unit 230 to determine the physical activity level of the patient. Many schemes are known for extracting from a motion sensor generated signal information relating to the physical activity level of a patient, and any such scheme can be used by processing unit 230. As illustrated in FIG. 5, one useful scheme is to rectify output 228 with rectifier 510 and then integrate the rectified signal 512 using integrator 514 over a time period. This time period can be a predetermined, fixed period of time or it can be a variable period of time whose length depends on other physiological parameters. For example, the time period might be the time over which a predetermined number of R waves are sensed in the heart.

Many other schemes exist for processing a signal created by a motion sensor to determine the physical activity level of a patient. An example of another such scheme involves determining the number of times that the activity level signal crosses a reference level during a predetermined time period. Any such other schemes may be used by processing unit 230 to process signal 228.

Figure 6:
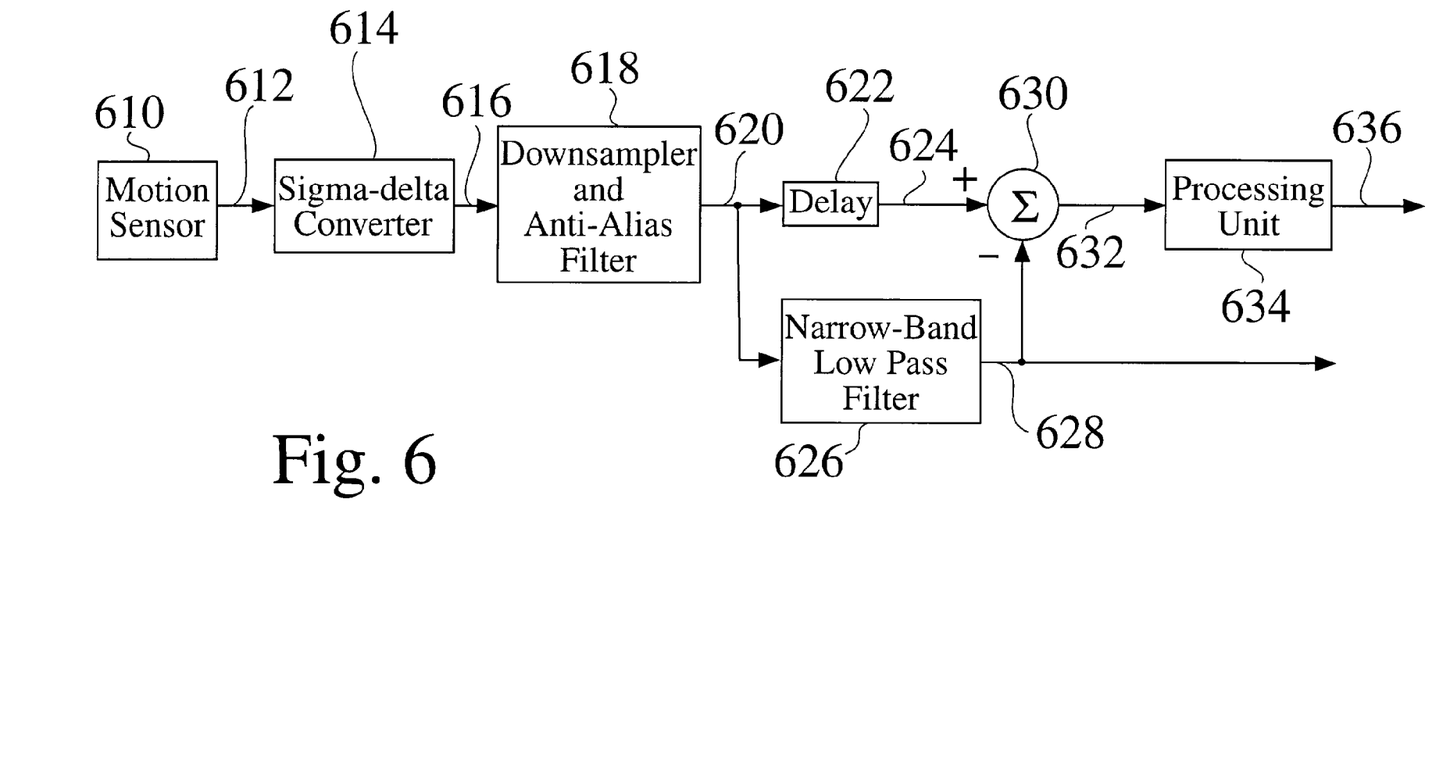
FIG. 6 illustrates another exemplary embodiment of the activity and position generator of FIG. 1.

FIG. 6 illustrates another exemplary embodiment of the activity and position generator 110. This embodiment includes a motion sensor 610 that, like the embodiment illustrated in FIG. 2, generates a composite signal 612 that includes information relating to both the position of the patient and the activity level of the patient. Any of the motion sensors described above with respect to FIG. 2 can be used in the embodiment of FIG. 6. A sigma-delta converter 614 processes the composite signal 612. As is known, a sigma-delta converter, in essence, acts as a high resolution analog to digital converter. Thus, the output 616 of the sigma-delta converter 614 is a high resolution, digital representation of the composite signal 612. As is also known, sigma-delta converters sometimes have the tendency to introduce artifacts due to digital sampling into a signal. Consequently, one or more downsamplers and anti-alias filters 618 may be utilized to remove any such artifacts from the signal 616 that were created by the 614 sigma-delta converter.

Preferably, the sigma-delta converter 614 is configured such that it performs a low pass filtering function and produces an output 616 that includes frequencies from the composite signal 612 in the range of approximately zero hertz to about ten hertz. For example, the downsampler and anti-alias filter 618 may include low pass filters whose output frequency response is about zero hertz to about ten hertz. A delay element 622 may be used to delay signal 620 so that it is input into an adder 630 at the same time as the output 628 of narrow-band low pass filter 626. Adder 630 may be similar to adder 226 described above with respect to FIG. 2. If sigma-delta converter 614 is not configured to covert only frequencies in the range of about zero hertz to about ten hertz in the composite signal 612, a low pass filter similar to low pass filter 218 should replace delay element 622.

Like signal 224 in FIG. 2, the output 628 of the narrow-band low pass filter 626 in FIG. 6 approximates the DC component of composite signal 612 created by motion sensor 610. As such it can be used to determine the position of the patient in which the pacemaker 100 is implanted. Signal 628 can be passed directly to the rate controller 116 as signal 112 in FIG. 1, or signal 628 can be further processed or combined with other signals before being passed to the rate controller 116. Also similar to the embodiment of FIG. 2, the output 632 of adder 630 can be processed by processing unit 634 in any of a number of different ways to extract useful information regarding the activity level of the patient.

Figure 7:
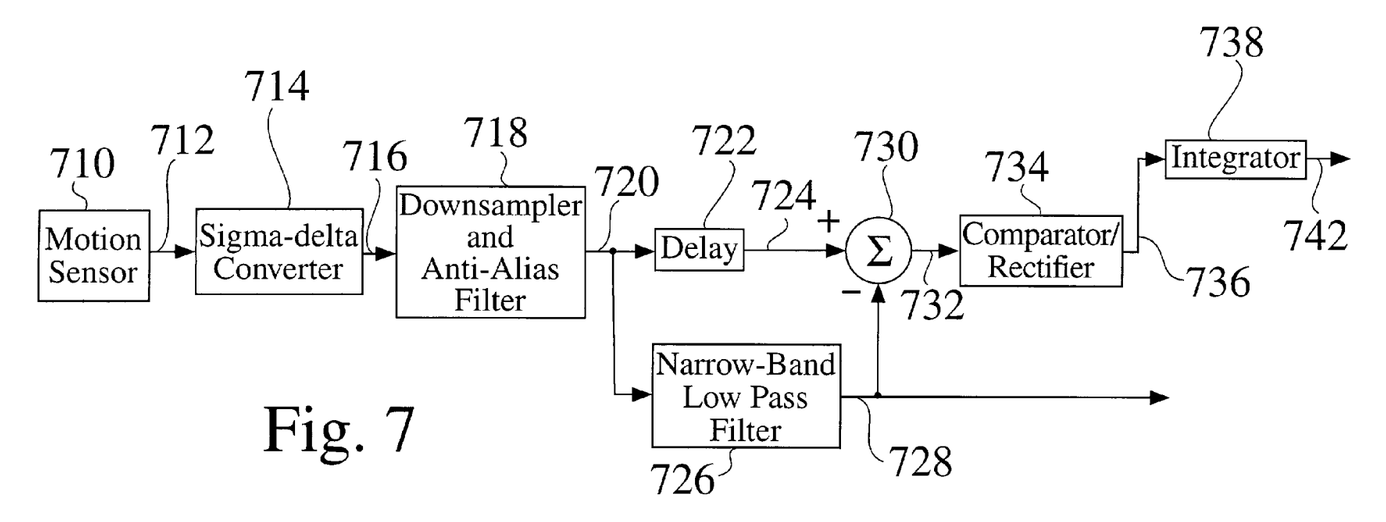
FIG. 7 illustrates a variation of the activity and position generator illustrated in FIG. 6.

FIG. 7 illustrates a variation of the embodiment illustrated in FIG. 6. The motion sensor 710, sigma-delta converter 714, one or more downsamplers and anti-alias filters 718, delay element 722, and narrow-band low pass filter 726 in FIG. 7 are similar to or the same as like-named elements in FIG. 6. Adder 730 in FIG. 7 is configured such that the subtraction of signal 728 from signal 724 always produces a positive number regardless of whether signal 728 is larger or smaller than signal 724. As is known in the art, this can be accomplished by using limited length registers in adder 730. In this way, higher order bits of the result of a subtraction of a signal 728 that is larger than signal 724 (and would therefore ordinarily produce a negative result) overflow the register and the resulting output of adder 730 is a positive number. In accordance with the number representation convention used at the output of the adder 730, a number that is less than half the maximum number allowed by the adder's register width represents a positive number while a number that is more than half the maximum number represents a negative number. A quality of this type of number representation is that when a number produced by addition or subtraction is too large or small to be represented by the limited register length, the value represented overflows to the opposite extreme. This is known in the art as either offset binary or two's complement number representation. Because of the limited length of the registers of the adder 730, the output 732 is partially rectified. That is, where input signal 724 is greater than input signal 728, all portions of the resulting output 732 of adder 730 are rectified. Comparator/rectifier 734 completes the rectification process by rectifying the portions of the output 732 signal that result from an input signal 724 that is less than input signal 728. Comparator/rectifier 736 rectifies only those portions of output 732 whose value exceeds one half of the length of the registers of adder 730. The output 736 of comparator/rectifier 734 is then integrated over a predetermined time period by integrator 738. The output 742 of the integrator 738 represents an approximation of the activity level of the patient during the predetermined time period, and the output 742 can be passed directly to the rate controller 116 as signal 114 or the output 742 can be further processed before being passed to the rate controller.

Figures 8A, 8B:
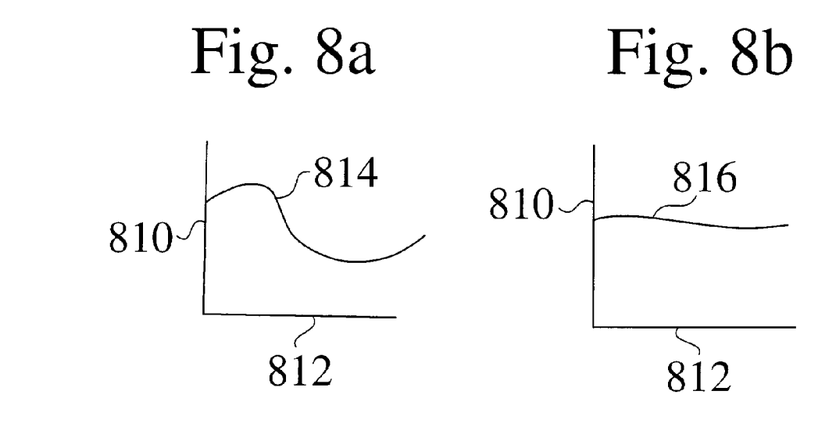
FIGS. 8*a* through 8*e* illustrate exemplary waveforms of signals at various points in the block diagram of FIG. 7.
Figure 8C:
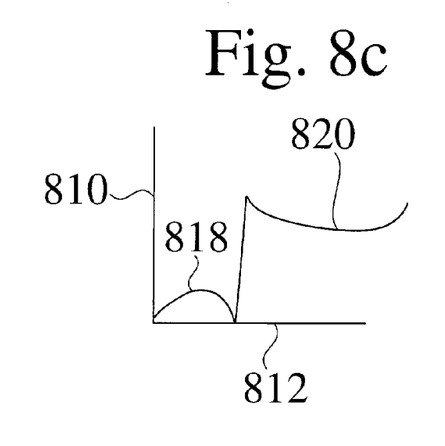
Figure 8D:
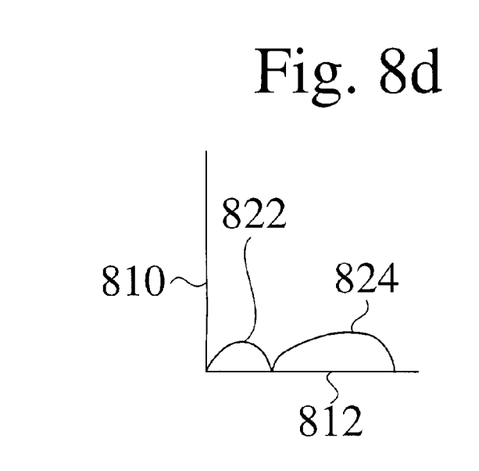
Figure 8E:
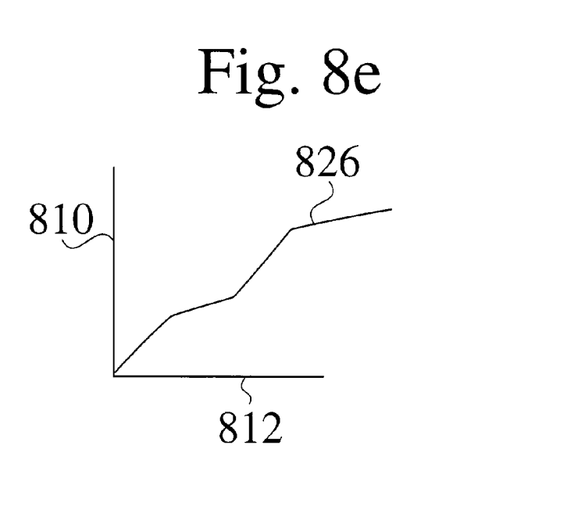

FIGS. 8a through 8e represent exemplary waveforms produced by the embodiment illustrated in FIG. 7. In each of FIGS. 8a through 8e, axis 810 represents the amplitude of the illustrated waveform, and axis 812 represents time. FIG. 8a represents an exemplary waveform 814 of signal 720, which is a digital representation of the composite signal 712 created by motion sensor 712. The waveform 816 shown in FIG. 8b represents the output 728 of the narrow-band low pass filter 726. As such, waveform 816 approximates the DC component of waveform 814. The waveform 818, 820 of FIG. 8c represents the output of adder 730 in which the waveform 816 is subtracted from the waveform 814. Because the waveform 816 is an approximation of the DC component of the waveform 814 and the first portion of waveform 814 is greater than waveform 816, the first portion 818 of the waveform of FIG. 8c is simply the first portion of the waveform 814 translated downward to axis 812. Because the second portion of waveform 814 is less than waveform 816, the result of subtracting waveform 816 from the second portion of waveform 814 would normally yield a negative number. As discussed above, however, subtraction of a larger number from a small number in adder 730 causes the most significant bits of the result to overflow the registers within the adder. The output 732 of adder 730 therefore are fairly large positive results, as shown by the second portion 820 of the waveform of FIG. 8c. The waveform 822, 824 of FIG. 8d represents the output 736 of comparator/rectifier 734. As discussed above, comparator/rectifier 734 rectifies the second potion 820 of the waveform. The waveform 826 of FIG. 8e is the integration of the waveform 822, 824. As such it represents the output 742 of integrator 738 when the waveform 822, 824 is input 736 into integrator 738.

The above described embodiments of the invention are not intended to be limiting. Persons skilled in the art will appreciate that modifications may be made to the these embodiments and alternative embodiments may be created that are within the scope and spirit of the invention. For example, although the low pass filters, sigma-delta converters, and/or anti-alias filters described above pass frequencies in the range of about zero hertz to about ten hertz, these elements can be changed to pass different frequency ranges, such as about zero hertz to about twenty or thirty hertz. Similarly, the frequency response of the narrow-band low pass filters described above could be changed to pass different frequency ranges, including about zero hertz to about one or two hertz.

What is claimed is:

1. A method for separating information representing position of a patient from information representing the patient's level of activity in a composite signal, said method comprising:
   sigma-delta converting said composite signal into a digitized composite signal;
   filtering said digitized composite signal to produce a filtered signal, wherein said filtered signal includes information from said composite signal representing the patient's position; and
   subtracting said filtered signal from said digitized composite signal to produce a difference signal, wherein said difference signal includes information from said composite signal representing the patient's level of activity.

2. The method of claim 1, further comprising:
   rectifying said difference signal to produce a rectified difference signal; and
   integrating said rectified difference signal.

3. The method of claim 1, wherein said filtering passes frequencies in a range of about zero hertz to about 0.5 hertz.

4. The method of claim 1, wherein said filtering passes frequencies in a range of about zero hertz to about one hertz.

5. An apparatus for separating information representing position of a patient from information representing the patient's level of activity in a composite signal, said apparatus comprising:
   converting means for converting said composite signal to digital format to produce a digitized composite signal;
   filtering means for filtering said digitized composite signal to produce a filtered digitized composite signal, wherein said filtered digitized composite signal includes information from said composite signal representing the patient's position; and
   subtracting means for subtracting said filtered digitized composite signal from said digitized composite signal to produce a difference signal, wherein said difference signal includes information representing the patient's level of activity.

6. The apparatus of claim 5, wherein said converting means comprises a sigma-delta converter.

7. The apparatus of claim 6, wherein said sigma-delta converter has a frequency response of about zero hertz to about ten hertz, and said filtering means has a frequency response of about zero hertz to about 0.5 hertz.

8. The apparatus of claim 6, wherein said sigma-delta converter has a frequency response of about zero hertz to about twenty hertz, and said filtering means has a frequency response of about zero hertz to about one hertz.

9. The apparatus of claim 5, wherein said converting means comprises an analog to digital converter and a low pass filter.

10. The apparatus of claim 9, wherein said low pass filter has a frequency response of about zero hertz to about ten hertz, and said filtering means has a frequency response of about zero hertz to about 0.5 hertz.

11. The apparatus of claim 9, wherein said low pass filter has a frequency response of about zero hertz to about twenty hertz, and said filtering means has a frequency response of about zero hertz to about one hertz.

12. The apparatus of claim 5, further comprising means for generating said composite signal.

13. An apparatus for separating information representing position of a patient from information representing the patient's level of activity in a composite signal, said apparatus comprising:
   a sigma-delta converter configured to receive as an input said composite signal;
   a filter configured to receive as an input an output of said sigma-delta converter, wherein an output of said filter includes information from said composite signal representing the patient's position; and
   an adder configured to subtract said output of said filter from said output of said sigma-delta converter, wherein an output of said adder includes information from said composite signal representing the patient's level of activity.

14. The apparatus of claim 13, further comprising a motion sensor for generating said composite signal.

15. The apparatus of claim 14, wherein said motion sensor comprises a microelectomechanical system.

16. The apparatus of claim 14, wherein said motion sensor comprises an accelerometer.

17. The apparatus of claim 13, wherein a data capacity of said adder is sufficiently limited that subtraction of a positive number from a smaller positive number produces a positive number.

18. The apparatus of claim 17, further comprising:
   a rectifier configured to receive as an input said output of said adder; and
   an integrator configured to receive as an input an output of said rectifier.

19. The apparatus of claim 18, wherein said rectifier includes a comparator.

20. The apparatus of claim 13, wherein said frequency response of said filter is about zero hertz to about 0.5 hertz.

21. The apparatus of claim 13, wherein said frequency response of said filter is about zero hertz to about one hertz.

22. The apparatus of claim 13, wherein said sigma-delta converter has a frequency response of about zero hertz to about ten hertz.

23. The apparatus of claim 13, wherein said sigma-delta converter has a frequency response of about zero hertz to about twenty hertz.

* * * * *